United States Patent [19]
Asai et al.

[11] Patent Number: 5,137,957
[45] Date of Patent: Aug. 11, 1992

[54] METHOD OF PREPARING AN ANTIBACTERIAL POLYMER AND ITS APPLICATION

[75] Inventors: Tamio Asai; Yoshitsugu Maruhashi, both of Yokohama, Japan

[73] Assignee: Toyo Seikan Kaisha, Ltd., Tokyo, Japan

[21] Appl. No.: 667,391
[22] PCT Filed: Jul. 31, 1990
[86] PCT No.: PCT/JP90/00979
  § 371 Date: Apr. 17, 1991
  § 102(e) Date: Apr. 17, 1991
[87] PCT Pub. No.: WO91/02026
  PCT Pub. Date: Feb. 21, 1991

[30] Foreign Application Priority Data
  Jul. 31, 1989 [JP] Japan ................................. 1-196684

[51] Int. Cl.$^5$ ................................................ C08K 3/20
[52] U.S. Cl. ..................................... 524/403; 523/122
[58] Field of Search ........................ 523/122; 524/403

[56] References Cited
U.S. PATENT DOCUMENTS
5,049,592 9/1991 Kronstein ............................ 523/122

Primary Examiner—Paul R. Michl
Attorney, Agent, or Firm—Sughrue, Mion, Zinn, Macpeak & Seas

[57] ABSTRACT

A method of preparing an antibacterial polymer and application of the antibacterial polymer obtained by this method. A silver oxide and a thermoplastic copolymer that contains a unit consisting of ethylenically unsaturated carboxylic acid or an anhydride thereof and that can be melted upon heating, are mixed, melted and is kneaded in order to obtain a polymer that exhibits in combination the antibacterial property and the heat-processability or the heat-moldability. By making this polymer present on the inner surface of the packing containers, it is made possible to impart the antibacterial property without deteriorating the flavor retentivity for the contents.

5 Claims, 2 Drawing Sheets

METHOD OF PREPARING AN ANTIBACTERIAL POLYMER AND ITS APPLICATION

TECHNICAL FIELD

The present invention relates to a method preparing an antibacterial polymer and its application, and particularly to an antibacterial packing material using the same polymer.

BACKGROUND ART

It has long been known that compounds of silver exhibit antibacterial property. For instance, calcium carbonate to which silver is added has been extensively used for the sterilization of the dechlorinated tap water.

It has also been known that antibacterial property is exhibited by a polymer that contains silver acrylate and/or silver methacrylate as a structural unit. Japanese Patent Publication No. 43123/1983 discloses an antibacterial semi-permeable composed of the above polymer and a cellulose ester.

Furthermore, Japanese Laid-Open Patent Publication No. 154746/1988 discloses an antibacterial film composed of a synthetic resin which contains dispersed therein a hygroscopic agent and zeolite-type solid particles that hold metal ions such as silver ions that exhibit antibacterial action by the exchange of ions, the zeolite-type solid particles having a specific surface area of greater than 150 m$^2$/g and an SiO$_2$/Al$_2$O$_3$ molar ratio of smaller than 14.

According to the method of producing the antibacterial polymer of the former publication, the silver acrylate and/or the silver methacylate is polymerized, or silver nitrate is reacted with polyacrylic acid, polymethacrylic acid or a copolymer thereof. However, the antibacterial polymer that is obtained lacks thermal stability under dry heated conditions, and does not apparently lend itself for such applications as forming films by the heat treatment or forming containers through the heat-molding.

According to the method of blending the silver ion-exchanged zeolite in the resin disclosed in the latter publication, there remain problems in regard to producing the silver ion-exchanged zeolite and in regard to that the sterilizing power decreases if there exist silver oxides in the zeolite, though there is problem with regard to heat resistance. There still exists a problem in that the silver ion-exchanged zeolite is alkaline just as the zeolite is in general, and hence tends to hydrolyze the resin that is blended.

DISCLOSURE OF THE INVENTION

The present inventors have discovered the fact that a polymer having antibacterial property is obtained when a silver oxide and a thermoplastic copolymer that contains a unit consisting of ethylenically unsaturated carboxylic acid or an anhydride thereof and that can be melted upon heating, are melted and kneaded together, and that the polymer can be heat-treated or heat-molded making it possible to obtain a container having antibacterial property if the innermost layer of the container is formed by using this polymer.

That is, the object of the present invention is to provide an antibacterial polymer that has a combination of excellent antibacterial property and heat-moldability or heat-processability, and that can be produced cheaply and easily, as well as a method of preparing the same polymer.

Another object of the present invention is to provide an antibacterial packing material that is free from the above-mentioned defects inherent in the prior art, that exhibits excellent antibacterial action as well as excellent flavor retentivity for the contents.

According to the present invention, there is provided a method of preparing an antibacterial polymer comprising mixing a silver oxide and a thermoplastic copolymer that contains a unit consisting of ethylenically unsaturated carboxylic acid or an anhydride thereof and that can be melted upon heating, and then melting and kneading the mixture.

According to the present invention, furthermore, there is provided an antibacterial packing material wherein at least the inner surface layer of the packing material contains an antibacterial polymer that a formed by kneading a silver oxide and a thermoplastic copolymer that contains a unit consisting of ethylenically unsaturated carboxylic acid or an anhydride thereof and that can be melting upon heating, the antibacterial polymer containing at least a moiety of the silver oxide in the form of a silver salt.

BEST MODE FOR CARRYING OUT THE INVENTION

The present invention is based on the discovery that when a silver oxide and a thermoplastic copolymer that contains a unit consisting of ethylenically unsaturated carboxylic acid or an anhydride thereof and that can be melted upon heating are melted and kneaded together, the silver component is dispersed in, in comparison with the case where other polymers or silver compounds are used, the polymer very homogeneously and finely, the silver oxide component is at least partly inverted into a silver salt, and the obtained polymer exhibits excellent antibacterial property as well as resistance large enough to withstand the heat treatment at the time of heat-molding and coating.

In the present invention, first, it is important to use a thermoplastic copolymer that contains a unit (hereinafter referred to as acid unit) consisting of ethylenically unsaturated carboxylic acid or an anhydride thereof and that can be melted upon heating as a polymer, as well as to use a silver oxide as a silver component.

That is even when a polymer without containing the above acid unit is melted and blended with the silver oxide, the blend exhibits almost no antibacterial property and, further, the silver oxide is poorly dispersed in the polymer. The acid unit-containing polymer which is a copolymer that can be melted upon heating plays an important role for being kneaded together with the silver oxide, and further plays important roles for imparting heat-processability at the time of coating by which the blend can be used as a packing material and for imparting heat-moldability at the time of molding the packing material.

When other silver components such as silver acetate and the like are used, the antibacterial property is not exhibited to a satisfactory degree unless they are used in considerably large amounts compared with when the silver oxide is used. In this case, furthermore, it is difficult to homogeneously and finely disperse the silver component in the polymer matrix.

Figure 1:
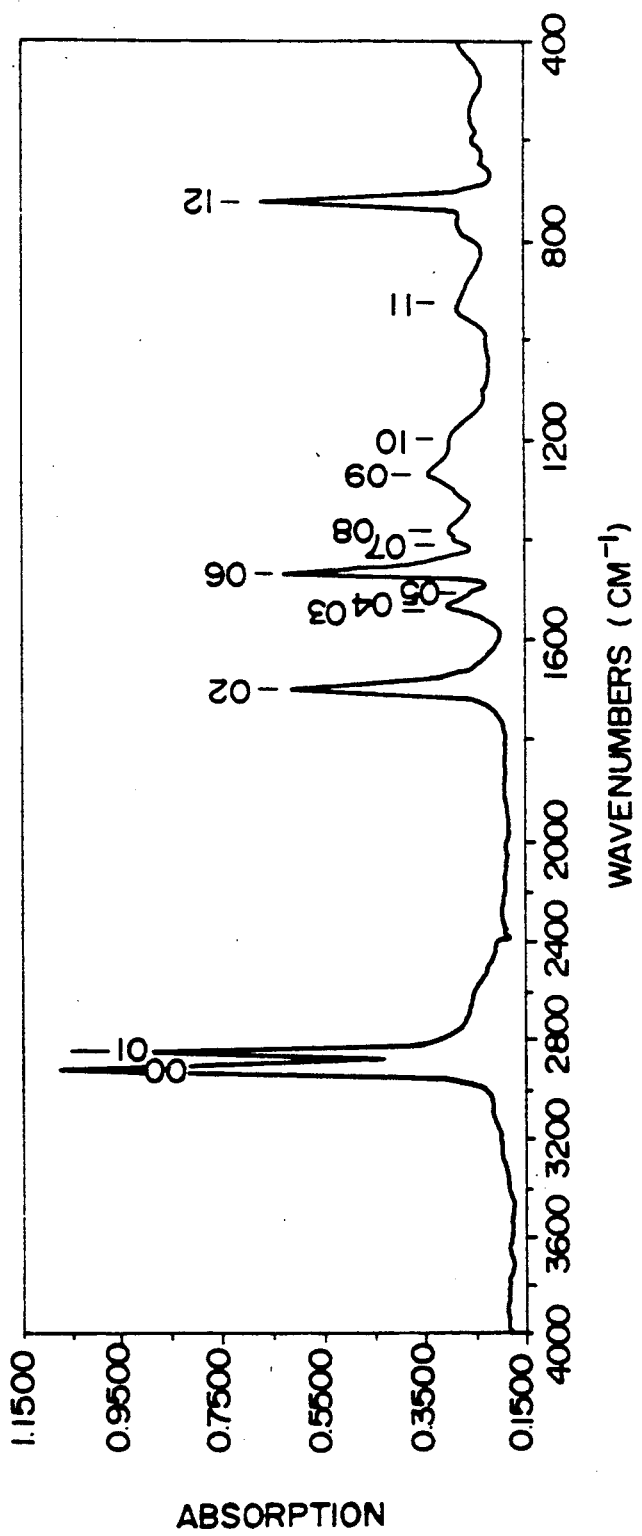
FIG. 1 is a diagram showing FI-IR spectra of an ethylene-methacrylic acid copolymer containing 3% by weight of silver oxide (Example 14)
Figure 2:
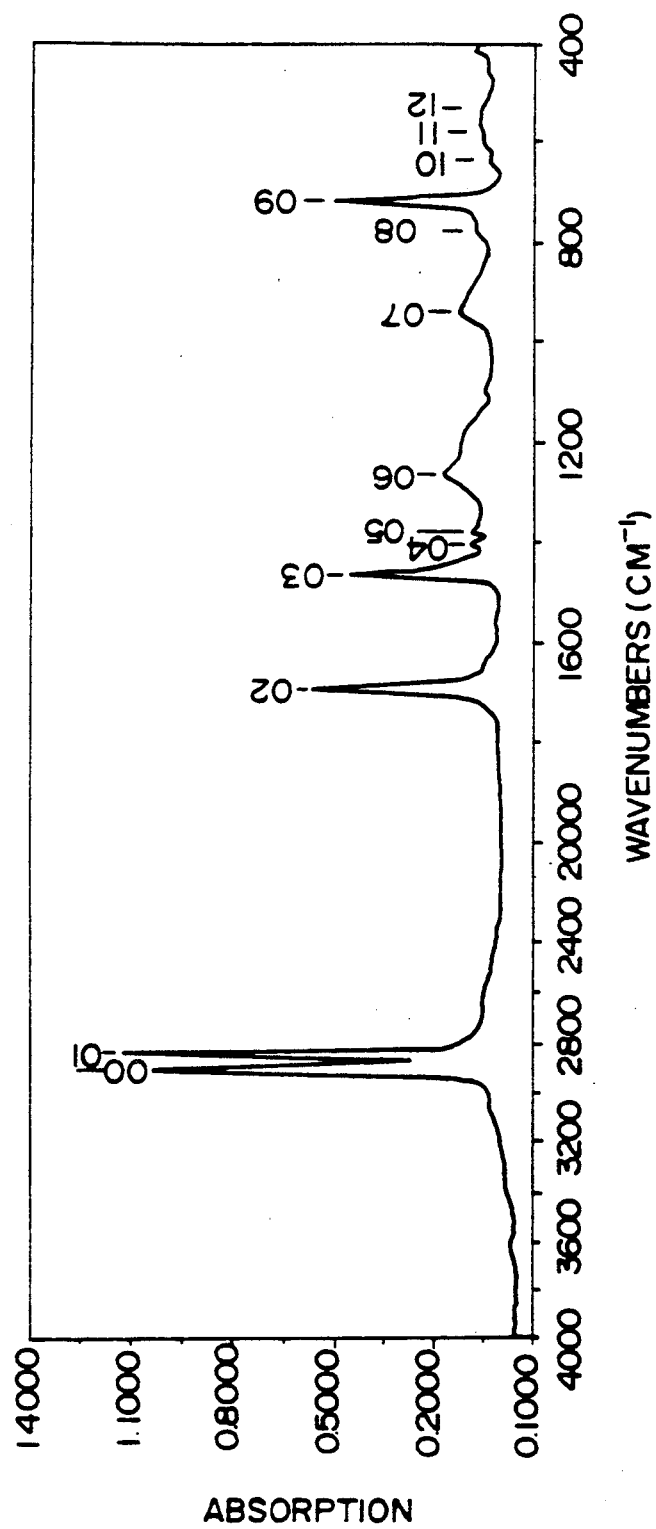
FIG. 2 is a diagram showing FI-IR spectra of an ethylene-methacrylic acid copolymer (Comparative Example 4).

When the copolymer containing the acid unit and the silver oxide are melted and kneaded together according to the present invention, at least moiety of the silver oxide is coupled to the acid unit to form a silver salt. This fact is confirmed from the measurement that the carboxyl group (—COOH) of acid unit in the copolymer is of the ionic type (—COO$^-$). The accompanying FIG. 2 is a diagram showing infrared-ray absorption spectra of a copolymer containing acid unit of a starting material of Example 4 that will be described later, and FIG. 1 is a diagram showing infrared-ray absorption spectra of a copolymer that is melted and kneaded together with the silver oxide. In the former case, the characteristic absorption of COOH is recognized near a wavenumber of 1697 cm$^{-1}$ but no characteristic absorption of COO$^-$ is recognized. In the latter case, the characteristic absorption of COO$^-$ appears at the wavenumbers 1530 to 1540 cm$^{-1}$ indicating the formation of a silver salt.

According to the present invention, the copolymer exhibits excellent antibacterial property being closely related to the fact that the silver component exists in the form of a salt that is coupled to the acid unit, and that the polymer contains the acid unit to permit the permeation of water that activates the silver component. This is in good agreement with the fact that almost no effect is exhibited by the polyethylene in which are blended silver oxide and silver acetate.

Besides, the copolymer that is kneaded together with the silver oxide does not give offensive taste or offensive odor to the packed content, but exhibits excellent flavor retentivity for the packed content and further exhibits antibacterial property.

According to the present invention, example of the acid unit of the copolymer include ethylenically unsaturated carboxylic acids such as methacrylic acid, acrylic acid, crotonic acid, itaconic acid, fumaric acid, maleic acid, anhydrous maleic acid and anhydrous itaconic acid, or anhydrides thereof, that are used alone or in a combination of two or more kinds. From the standpoint of thermal stability, it is preferred to use the acid unit consisting chiefly of methacrylic acid.

From the standpoint of melting property and thermal stability, the above acid unit must be a copolymer with a monomer constituting a polymer that has melt-moldability. The most preferred examples of such copolymers, are olefins such as ethylene, propylene, butene-1, pentene-1, and heptene-1. Among them, ethylene is preferred. Other copolymerizable monomers include vinyl-type or acrylic-type monomers such as styrene, vinyl chloride, (meth)acrylic acid ester, vinyl acetate and acrylonitrile.

The content of acid unit in the copolymer should generally range from 0.2 to 35 mole % and, preferably, from 2 to 25 mole % from the standpoint of both the antibacterial property and the thermal stability. Further, the copolymer that is used should have a melting point (or softening point when the melting point is not obvious) of generally 70° to 220° C., and particularly, 80° to 210° C. Furthermore, the molecular weight of the copolymer should lie within a range in which the films can be formed.

The copolymer which is particularly adapted to achieving the object of the present invention comprises ethylenically unsaturated carboxylic acid or an anhydride thereof in an amount of 0.2 to 35 mole % and, particularly, in an amount of 2 to 25 mole %, olefins in an amount of 65 to 99.8 mole % and, particularly, in an amount of 75 to 98 mole %, and (meth)acrylic acid ester in an amount of 0 to 35 mole % and, particularly, in an amount of 0 to 25 mole %.

The silver oxide should have a purity of higher than 98 % and, particularly, higher than 99 %, and a particle size which generally is as fine as 10 $\mu$m or smaller, and particularly 5 $\mu$m or smaller.

The amount of blending the silver oxide with respect to the copolymer should generally be from 0.0005 to 10 % by weight and, particularly, from 0.001 to 5 % by weight from the standpoint of cost, antibacterial property and dispersibility, though the amount may vary depending upon the applications and the required antibacterial property.

To prepare the antibacterial polymer, the copolymer and the silver oxide are pre-mixed by a method which is usually called dry blend. This enables the silver oxide to uniformly adhere on the surfaces of the copolymer particles. The pre-mixing can be effected by using a ribbon blender, a conical blender, the Henschel's mixer, a ball mill, or a super mixer.

The pre-mixture is then kneaded at a temperature which is higher than the melting temperature of the copolymer but is lower than the decomposition temperature of the copolymer. Usually, the kneading temperature should range from 90° to 220° C., and the kneading is preferably effected in an insert atmosphere such as in an nitrogen atmosphere using a monoaxial or biaxial extruder, a kneader, or the Bumbery's mixer. According to the present invention, the feature resides in that the kneading operation is carried out at a relatively low temperature in a short period of time, and at least moiety of the silver oxide is inverted into a silver salt through the kneading operation.

It is preferred that the silver component in the form of a silver salt is contained at a concentration of greater than $5 \times 10^{-3}$ milligram atoms and, particularly, $10^{-2}$ to 50 milligram atoms per 100 g of the copolymer.

The melted and kneaded product of the present invention is used for forming a packing material, by itself or in the form of a blend together with other plastic material for forming containers, or in the form of a composition together with a resin for forming coating or together with a coating material.

For instance, the above melted and kneaded product is subjected to the T-die method or the inflation film-forming method in order to obtain a film for packing and a sheet for forming containers. Further, the kneaded product is extruded through a circular die to form a Parison for blow-molding. The sheet is subjected to the vacuum molding, compressed-air molding or plug-assist molding in order to form plastic containers, and the Parison is blow-molded to form plastic containers having the shape of a bottle.

At the time of extrusion molding, a base resin layer such as of polyethylene, polypropylene or polyester and a layer of the kneaded copolymer of the present invention are allowed to meet together in the die, and are extruded together thereby to form a multi-layer film or a multi-layer plastic container.

Moreover, the antibacterial polymer film of the present invention that has been formed in advance is subjected together with other resin film or a metal foil or a combination thereof, to widely known means such as the sandwich lamination, dry lamination or extrusion coating method, in order to obtain a multi-layer film or a laminate for forming multi-layer containers.

Furthermore, the melting and kneaded product is fed to a pelletizer to pulverize it as required, or is dispersed in water to obtain antibacterial particles that will be used being dispersed in other resins or the coating materials.

The particles of the antibacterial polymer are blended in a molding polymer such as polyethylene, and are subjected to the same means as the one described above, in order to form single-layer or multi-layer plastic containers. The antibacterial polymer of the present invention can be blended in other polymers for molding in an amount of 1 to 80 % by weight and, particularly, in an amount of 5 to 80 % by weight.

Furthermore, the powder of the antibacterial polymer can be used for coating the inner surfaces of cans, caps, can lids and the like, being dispersed in the coating materials that are known per se for costing the inner surfaces of packing materials, such as epoxyphenol-type coating material epoxyamino-type coating material, vinyl-type coating material, acrylic-type coating material, phenol-type coating material, alkid-type coating material, and organosol-type coating material. In this case, the antibacterial polymer should have a particle size of from 0.1 to 10 $\mu$m and, particularly, from 0.1 to 5 $\mu$m, and should further be contained in an amount of 1 to 80 % by weight with respect to the solid component of the coating material.

The antibacterial polymer of the present invention can be contained in the liners and packings of the type of olefin resin or of the type of various elastomers fitted to the inner surfaces of the caps, or can be contained in the sealing gaskets and in the heat sealants for a variety of containers.

EMBODIMENTS

Described below are the embodiments of the present invention in which the effects of sterilization are evaluated in compliance with the following testing method.

Test for evaluating antibacterial property

A suspension of escherichia coli IAM1239 or staphylococcus aureus IAM12544 was so diluted that the test bacteria solution contained bacteria in a number of 2 to $4 \times 10^6$/ml. 0.1 Milliliter of the test bacteria solution was dropped on a sample cut in a size of $5 \times 5$ cm$^2$, and was held under this condition maintained at 37° C. for 24 hours. After 24 hours have passed, the sample was washed with 30 ml of physiological saline solution, and the number of living bacteria in the washing solution was measured by the membrane filter method. The culture was carried out using a bouillon culture ground for general bacteria (produced by Nissui Seiyaku Co.) at a temperature of 37° C. for 24 hours.

Resins used in the embodiments of the present invention are shown in Table 1 below.

TABLE 1

| Brief Designation | Resin monomer composition | | | Melting point |
|---|---|---|---|---|
| EO | 100 | % E | | 140° C. |
| EMO1 | 99.9 | % E/0.1 | % MAA | 130 |
| EM2 | 98 | % E/2 | % MAA | 110 |
| EM9 | 91 | % E/9 | % MAA | 96 |
| EM15 | 85 | % E/15 | % MAA | 85 |

TABLE 1-continued

| Brief Designation | Resin monomer composition | | | Melting point |
|---|---|---|---|---|
| EA9 | 91 | % E/9 | % AA | 100 |

E: ethylene
MAA: methacrylic acid
AA: acrylic acid

ANTIBACTERIAL MATERIALS

Examples 1, 2, 3 and 4

An ethylene-methacrylic acid copolymer EM9 was mixed with 0.003 to 3% by weight of a silver oxide using a mixer at a mixing temperature of 150° C. The mixture was then heated and pressed by a hot-press machine at 200° C. for two minutes to obtain a film having a thickness of 50 $\mu$m.

Ethylene-methacrylic acid copolymers EM2, EM9, EM15 and ethylene-acrylic acid copolymer EA9 were, respectively, mixed with 0.05% by weight of the silver oxide using the mixer at a mixing temperature of 150° C. The mixture were then heated and pressed by the hot-press machine at 200° C. for two minutes to obtain films all having of 50 $\mu$m.

COMPARATIVE EXAMPLES 1, 2, 3, 4, 5 and 6

The resins of Table 1 were heated and pressed by the hot-press machine at 200° C. for two minutes to obtain films all having a thickness of 50 $\mu$m.

COMPARATIVE EXAMPLE 7

The ethylene-methacrylic acid copolymer EM9 was mixed with 0.0003 by weight of the silver oxide in the same manner as the above examples to obtain a film.

COMPARATIVE EXAMPLES 8, 9 and 10

The ethylene-methacrylic acid copolymer EM9 was mixed with 1% by weight of a silver powder (325 mesh), silver chloride or silver acetate using a mixer at a mixing temperature of 150° C. The mixtures were then heated and pressed using the hot-press machine at 200° C. for two minutes to obtain films all having a thickness of 50 $\mu$m.

Note) Comparative Example 10 exhibits antibacterial property emitting, however, the odor of acetic acid. The prepared film emits the odor of acetic acid, too, lending itself not for being used as a packing material.

EXAMPLES 5, 6, 7 and 8

The ethylene-methacrylic acid copolymer EM9 was mixed with 0.1% by weight of the silver oxide using the mixer at mixing temperatures of 125° C., 150° C., 175° C. and 200° C. The mixture were heated and pressed by the hotpress machine at 200° C. for two minutes to obtain films all having of 50 $\mu$m.

COMPARATIVE EXAMPLE 11

The ethylene-methacrylic acid copolymer EM9 was mixed with 0.1% by weight of the silver oxide using the mixer at a mixing temperature of 225° C. The mixture was heated and pressed by the hot-press machine at 200° C. for two minutes to obtain a film having a thickness of 50 $\mu$m.

COMPARATIVE EXAMPLE 12

The polyethylene EO was mixed with 1% by weight of the silver oxide using the mixer at a mixing temperature of 170° C. The mixture was then heated and pressed by the hot-press machine at 200° C. for two minutes to obtain a film having a thickness of 50 μm.

COMPARATIVE EXAMPLE 13

The ethylene-methacrylic acid copolymer EM01 was mixed with 0.1% by weight of the silver oxide using the mixer at a mixing temperature of 170° C. The mixture was then heated and pressed by the hot-press machine at 200° C. for two minutes to obtain a film having a thickness of 50 μm.

Table 2 shows the results of antibacterial test of the samples.

EXAMPLES 13, 14, 15 and 16

A polyethylene (density 0.92) (simply referred to as E1) was mixed with the above mixture K1 in an amount of 5 to 50% by weight using the mixer at a mixing temperature of 170° C., and was heated and pressed by the hot-press machine at 200° C. for two minutes to obtain a film having a thickness of 50 μm.

COMPARATIVE EXAMPLE 14

The polyethylene E1 was mixed with the above mixture K1 in an amount of 1% by weight using the mixer at a mixing temperature of 170° C., and was heated and

TABLE 2

| | Resin | Kind | Content of silver compound (wt %) | Mixing temp. (°C.) | Antibacterial test (Escherichia coli) Number of living bacteria/25 cm$^2$ (Preserved of 37° C. for 24 hours) | (Staphylococcus aureus) Number of living bacteria/25 cm$^2$ (Preserved of 37° C. for 24 hours) |
|---|---|---|---|---|---|---|
| Comp. Example | | | | | | |
| 1 | EO | — | | | $5.0 \times 10^5$ | $3.7 \times 10^5$ |
| 2 | EMO1 | — | | | $1.9 \times 10^5$ | $2.5 \times 10^5$ |
| 3 | EM2 | — | | | $4.1 \times 10^5$ | $2.0 \times 10^5$ |
| 4 | EM9 | — | | | $2.8 \times 10^5$ | $4.0 \times 10^5$ |
| 5 | EM15 | — | | | $5.7 \times 10^5$ | $4.3 \times 10^5$ |
| 6 | EM9 | — | | | $3.0 \times 10^5$ | $4.5 \times 10^5$ |
| Example | | | | | | |
| 1 | EM9 | Ag$_2$O | 0.003 | 150 | $8.0 \times 10^3$ | $5.0 \times 10^3$ |
| 2 | | | 0.03 | 150 | <30 | <30 |
| 3 | | | 0.3 | 150 | <30 | <30 |
| 4 | | | 3.0 | 150 | <30 | <30 |
| Comp. Example | | | | | | |
| 7 | EM9 | Ag$_2$O | 0.0003 | 150 | $2.0 \times 10^5$ | $4.0 \times 10^5$ |
| 8 | EM9 | Ag | 1 | 150 | $4.2 \times 10^5$ | $3.1 \times 10^5$ |
| 9 | | AgCl | 1 | 150 | $3.7 \times 10^5$ | $4.0 \times 10^5$ |
| 10 | | AgAc | 1 | 150 | 30 | <30 *) |
| Example | | | | | | |
| 5 | EM9 | Ag$_2$O | 0.05 | 125 | <30 | <30 |
| 6 | | Ag$_2$O | 0.05 | 150 | <30 | <30 |
| 7 | | Ag$_2$O | 0.05 | 175 | <30 | <30 |
| 8 | | Ag$_2$O | 0.05 | 200 | $7.1 \times 10^3$ | $3.0 \times 10^3$ |
| Comp. Example | | | | | | |
| 11 | EM9 | Ag$_2$O | 0.05 | 225 | $4.5 \times 10^5$ | $2.8 \times 10^5$ |
| Example | | | | | | |
| 9 | EM2 | Ag$_2$O | 0.1 | 170 | $5.0 \times 10^3$ | $1.8 \times 10^3$ |
| 10 | EM9 | Ag$_2$O | 0.1 | 170 | <30 | <30 |
| 11 | EM15 | Ag$_2$O | 0.1 | 170 | <30 | <30 |
| 12 | EM9 | Ag$_2$O | 0.1 | 170 | <30 | <30 |
| Comp. Example | | | | | | |
| 12 | EO | Ag$_2$O | 0.1 | 170 | $3.1 \times 10^5$ | $4.3 \times 10^5$ |
| 13 | EMO1 | Ag$_2$O | 0.1 | 170 | $4.4 \times 10^5$ | $1.7 \times 10^5$ |

BLEND

The ethylene-methacrylic acid copolymer EM9 was mixed with 0.3% by weight of the silver oxide using the mixer at a mixing temperature of 150° C. to obtain a mixture which is hereinafter referred to as K1.

pressed by the hot-press machine at 200° C. for two minutes to obtain a film having a thickness of 50μm. Comparative Example 15, 16, 17 and 18.

The polyethylene E1 was mixed with a resin EM3 in an amount of 5 to 50% by weight using the mixer at a mixing temperature of 170° C., and was heated and pressed by the hot-press machine at 200° C. for two minutes to obtain a film having a thickness of 50μm.

Table 3 shows the results of antibacterial test of the samples.

TABLE 3

| | Resin | (%) | (%) | Mixing temp. (°C.) | Antibacterial test (Escherichia coli) Number of living bacteria/25 cm$^2$ (Preserved at 37° C. for 24 hours) | (Staphylococcus aureus) Number of living bacteria/25 cm$^2$ (Preserved at 37° C. for 24 hours) |
|---|---|---|---|---|---|---|
| Example | | | | | | |
| 13 | KI | 5/EI | 95 | 170 | $3.7 \times 10^4$ | $8.4 \times 10^4$ |
| 14 | | 10 | 90 | | $8.8 \times 10^2$ | $1.8 \times 10^3$ |
| 15 | | 30 | 70 | | <30 | <30 |
| 16 | | 50 | 50 | | <30 | <30 |
| Comparative Example | | | | | | |
| 14 | KI | 1/EI | 99 | 170 | $2.5 \times 10^5$ | $1.0 \times 10^5$ |
| 15 | EM3 | 5/EI | 95 | 170 | $2.8 \times 10^5$ | $4.0 \times 10^5$ |
| 16 | | 10 | 90 | | $1.3 \times 10^5$ | $3.7 \times 10^5$ |
| 17 | | 30 | 70 | | $4.2 \times 10^5$ | $3.0 \times 10^5$ |
| 18 | | 50 | 50 | | $4.5 \times 10^5$ | $2.9 \times 10^5$ |

COATING MATERIAL

The powder used for the examples was prepared as described below.

The ethylene-methacrylic acid copolymer EM9 was admixed with 0.3% by weight of the silver oxide, extruded by a monoaxial extruder at 150° C., and was pelletized. The pellets were pulverized into a powdery form. The granules having sizes of smaller than 10 μm were separated and used for the experiment. The granules having sizes of smaller than 10 μm were separated and used for the experiment. The granules are hereinafter simply referred to as PK1.

The pellets of ethylene-methacrylic acid copolymer EM9 were similarly pulverized and separated. The granules thereof are simply referred to as PEM. Examples 17, 18, 19 and 20.

In the epoxyphenol-type coating material was dispersed the above powder PK1 in an amount of 5 to 50% by weight with respect to the solid content. Then, the coating material was applied using a bar coater onto a steel plate (0.18 mm thick) that has been electrolytically plated with chromium, and was heated and dry-baked in a gas oven at 200° C. for one minute. The dry film possessed a thickness of about 20 μm.

and was heated and dry-baked in the gas oven at 200° C. for one minute. The dry film possessed a thickness of about 29 μm.

COMPARATIVE EXAMPLE 20

In the epoxyphenol-type coating material was dispersed the above powder PK1 in an amount of 1% by weight with respect to the solid content. Then, the coating material was applied using a bar coater onto the steel plate (0.18 mm thick) the has been electrolytically plated with chromium, and was heated and dry-baked in the gas oven at 200° C. for one minute. The dry film possessed a thickness of about 20 μm.

COMPARATIVE EXAMPLES 21, 22, 23, 24 and 25

In the epoxyphenol-type coating material was dispersed the above powder PEM in an amount of 1 to 50% by weight with respect to the solid content. Then, the coating material was applied using a bar coater onto the steel plate (0.18 mm thick) that has been electrolytically plated with chromium, and was heated and dry-baked in the gas oven at 200° C. for one minute. The dry film possessed a thickness of about 20 μm.

The bacterial tests were carried out in the same manner as the case of the films by cutting the coated plates into 5×5 cm$^2$. The results were as shown in Table 4.

TABLE 4

Paint: epoxyphenol

| | | Amount of powder blended | Antibacterial test (Escherichia coli) Number of living bacteria/25 cm$^2$ (Preserved at 37° C. for 24 hours) | (Staphylococcus aureus) Number of living bacteria/25 cm$^2$ (Preserved at 37° C. for 24 hours) |
|---|---|---|---|---|
| Example | | | | |
| 17 | PK1 | 5% | $5.6 \times 10^4$ | $8.1 \times 10^4$ |
| 18 | | 15% | $7.1 \times 10^2$ | $1.2 \times 10^3$ |
| 19 | | 25% | <30 | <30 |
| 20 | | 50% | <30 | <30 |
| Comparative Example | | | | |
| 19 | | 1% | $4.3 \times 10^5$ | $3.9 \times 10^5$ |
| 20 | PK1 | 1% | $3.5 \times 10^5$ | $6.1 \times 10^5$ |
| 21 | PEM | 1% | $6.0 \times 10^5$ | $5.1 \times 10^5$ |
| 22 | | 5% | $5.3 \times 10^5$ | $4.8 \times 10^5$ |
| 23 | | 15% | $4.7 \times 10^5$ | $3.3 \times 10^5$ |
| 24 | | 25% | $4.2 \times 10^5$ | $6.9 \times 10^5$ |
| 25 | | 50% | $5.1 \times 10^5$ | $3.5 \times 10^5$ |

COMPARATIVE EXAMPLE 19

The epoxyphenol-type coating material was applied using a bar coater onto the steel plate (0.18 mm thick) that has been electrolytically plated with chromium,

EXAMPLE 21

The ethylene-methacrylic acid copolymer (methacrylic acid, 9 mole %) was mixed with 0.05% by weight of the silver oxide, and was pelletized (EM9 (0.05 Ag$_2$O)) by using the monoaxial extruder. The pellets and polypropylene were extruded together to form a multi-layer sheet. The multi-layer sheet consisting of an inner layer EM9 (0.05 Ag$_2$O) 10 μm thick and an outer layer PP 800 μm thick was molded into a round cup (having a flange diameter of 80 mm, an inner diameter of 70 mm and a depth of 35 mm) through the molten compressed-air molding.

The antibacterial test was carried out as described below.

A test bacteria solution of escherichia coli or staphylococcus sureus that has been so diluted that the number of bacteria was 2 to 4×10$^6$/ml was dropped in an amount of 0.1 ml on the inner surface of the cup and was maintained under this condition at 37° C. for 24 hours. After 24 hours have passed, the inner surface of the cup was washed with 30 ml of physiological saline solution, and the number of living bacteria in the washing solution was measured by the membrane filter method. The culture was carried out using a bouillon culture ground for general bacteria (produced by Nissui Seiyaku Co.) at a temperature of 37° C. for 24 hours.

Table 5 shows the results of the antibacterial test.

TABLE 5*

| Antibacterial test. | |
|---|---|
| | Number of living bacteria/cup (37° C. × 24 hours) |
| Escherichia coli | 30 |
| Staphylococcus aureus | 30 |

According to the present invention as is obvious from the foregoing embodiments, a thermoplastic copolymer the contains s unit consisting of ethylenically unsaturated carboxylic acid or an anhydride thereof and that can be melted upon heating and a silver oxide are mixed together and are kneaded, in order to form a polymer that exhibits in combination the antibacterial property and the heat-processability or the heat-moldability. By making the polymer present on the surfaces of the containers for packing, it is made possible to impart the antibacterial property without deteriorating the flavor retentivity for the contents. The containers can be advantageously used as an aseptic packing route or as containers for packing fresh foods without requiring and particular sterilization operation.

We claim:

1. A method of preparing an antibacterial polymer comprising mixing a silver oxide and a thermoplastic copolymer that contains a unit consisting of ethylenically unsaturated carboxylic acid or an anhydride thereof and that can be melted upon heating, and then melting and kneading the mixture.

2. A method of preparing an antibacterial polymer according to claim 1, wherein said thermoplastic copolymer contains an ethylenically unsaturated carboxylic acid or an anhydride thereof in an amount of 0.2 to 35 mole %, an olefin in an amount of 65 to 99.8 mole %, and an ethylenically unsaturated carboxylic acid ester in an amount of 0 to 30 mole %.

3. A method of preparing an antibacterial polymer according to claim 1, wherein the silver oxide is mixed in an amount of 0.0005 to 10 % by weight with respect to said copolymer.

4. An antibacterial packing material wherein at least the inner surface layer of the packing material contains an antibacterial polymer that is formed by kneading a silver oxide and a thermoplastic copolymer that contains a unit consisting of an ethylenically unsaturated carboxylic acid or an anhydride thereof and that can be melted upon heating, the antibacterial polymer containing at least a moiety of the silver oxide in the form of a silver salt.

5. A coating material to be applied to the inner surface of a packing material wherein said coating material contains dispersed therein an antibacterial polymer that is formed by kneading a silver oxide and a thermoplastic copolymer that contains a unit consisting of an ethylenically unsaturated carboxylic acid or an anhydride thereof and that can be melted upon heating, the antibacterial polymer containing at least a moiety of the silver oxide in the form of a silver salt.

* * * * *